US006779383B2

(12) United States Patent
Lizotte et al.

(10) Patent No.: US 6,779,383 B2
(45) Date of Patent: Aug. 24, 2004

(54) WIPER AND BRUSH DEVICE FOR CLEANING WATER QUALITY SENSORS

(75) Inventors: Mike Lizotte, Marion, MA (US); Chris Hoffman, Yellow Springs, OH (US); Daniel Lechleiter, Indianapolis, IN (US); John McDonald, Fairborn, OH (US)

(73) Assignee: YSI Incorporated, Yellow Springs, OH (US)

( * ) Notice: Subject to any disclaimer, the term of this patent is extended or adjusted under 35 U.S.C. 154(b) by 2 days.

(21) Appl. No.: 10/388,368

(22) Filed: Mar. 13, 2003

(65) Prior Publication Data

US 2003/0233723 A1 Dec. 25, 2003

Related U.S. Application Data

(60) Provisional application No. 60/364,951, filed on Mar. 15, 2002.

(51) Int. Cl.[7] .............................................. G01N 21/00
(52) U.S. Cl. ..................................................... 73/61.48
(58) Field of Search ......................... 73/61.48; 250/431

(56) References Cited

U.S. PATENT DOCUMENTS

| | | | | |
|---|---|---|---|---|
| 3,844,661 A | * | 10/1974 | Birkett et al. ................ | 356/414 |
| 4,562,735 A | * | 1/1986 | Krippner et al. ........... | 73/865.8 |
| 4,701,959 A | | 10/1987 | Asai et al. | |
| 4,896,047 A | * | 1/1990 | Weaver et al. .............. | 250/573 |
| 5,099,115 A | * | 3/1992 | Cruickshank ............... | 250/236 |
| 5,185,531 A | * | 2/1993 | Wynn ......................... | 250/431 |
| 5,245,200 A | | 9/1993 | Fladda | |
| 6,111,249 A | | 8/2000 | Garner, III | |
| 6,121,053 A | * | 9/2000 | Kolber et al. ................ | 436/172 |
| 6,218,662 B1 | * | 4/2001 | Tchakarov et al. .......... | 250/256 |
| 2003/0177851 A1 | * | 9/2003 | Henry et al. ................ | 73/866.5 |

FOREIGN PATENT DOCUMENTS

| | | | | |
|---|---|---|---|---|
| GB | 2295232 | | 5/1996 | |
| JP | 05159339 A | * | 6/1993 | ............ G11B/7/12 |

OTHER PUBLICATIONS

Specification Sheet for "YSI 6025 Chlorophyll Sensor," website of YSI Environmental (Jul. 15, 2003).
Specification Sheet for "YSI 6130 Rhodamine WT Sensor," website of YSI Environmental (Jul. 15, 2003).
Specification Sheet for "YSI 6136 Turbidity Sensor," website of YSI Environmental (Jul. 15, 2003).
"Probe Wiper Agitator," website of Point Four Systems Inc. (Jul. 17, 2003).
Patent Abstracts of Japan, vol. 1999, No. 04 (Apr. 30, 1999) and JP 11 014540 A (Suido Kiko Kaisha Ltd.) (Jan. 22, 1999).
Patent Abstracts of Japan, vol. 2000, No. 01 (Jan. 31, 2000) and JP 11 287751 A (Shinko Electric Co. Ltd.) (Oct. 19, 1999).
Patent Abstracts of Japan, vol. 009, No. 289 (P–405) (Nov. 15, 1985) and JP 60 128333 A (Hitachi Seisakusho KK) *Jul. 9, 1985).
Patent Abstracts of Japan, vol. 1996, No. 01 (Jan. 31, 1996) and JP 07 243964 A (Doriko KK) (Sep. 19, 1995).

* cited by examiner

*Primary Examiner*—Hezron Williams
*Assistant Examiner*—Charles D Garber
(74) *Attorney, Agent, or Firm*—Thompson Hine LLP

(57) ABSTRACT

A sonde comprising a first sensor and a second sensor adjacent the first sensor, the first sensor including an optical window and a wiper element, the wiper element rotating on a shaft extending from the first sensor so as to clean debris from the window, a brush extending from the wiper element beyond the perimeter of the first sensor such that the brush contacts the adjacent second sensor and removes debris which accumulates on the second sensor.

18 Claims, 1 Drawing Sheet

WIPER AND BRUSH DEVICE FOR CLEANING WATER QUALITY SENSORS

CROSS-REFERENCE TO RELATED APPLICATIONS

This application claims priority from U.S. Provisional Application No. 60/364,951 filed Mar. 15, 2002.

BACKGROUND

Sensor devices or sondes are used for measuring the quality of water. A sonde can contain several different water quality probes or sensors including sensors for turbidity, pH, dissolved oxygen, conductivity, temperature, salinity and possibly other water quality measurements. These measurements are typically made using optical and/or electrical means. If the optical pathway or the electrical contacts become contaminated with debris or fungal or algal growth, inaccurate measurements may be obtained.

It is known in the art to equip these sondes with sensors that include an optical window through which measurements are made as a function of reflectance, fluorescence or another optical or photosensitive response. However, in measurements involving extended, long-term deployments, extensive fouling by plant and animal species may accumulate onto the sensor, thereby preventing the sensors from making accurate measurements. Thus, this fouling limits present sensors to be used for short periods only before maintenance or manual clean-up is required. Furthermore, in aggressive fouling environments, the accumulation of debris or fungal or algal growth onto the sensors may result in a short period of time. Present sensors are not properly equipped to obtain accurate measurements in severe fouling environments for an extended period of time.

It is therefore desirable to provide a sensor device which may be used effectively and obtain accurate measurements in both extended, long-term deployments and also aggressive fouling environments.

SUMMARY OF THE INVENTION

This invention is directed to a sensor cleaning apparatus useful in obtaining accurate measurements for measuring multiple parameters of the quality of water in extended, long-term deployments and in aggressive fouling environments.

The sensor cleaning apparatus comprises a sonde having a sensor, a wiper element and a brush, wherein the brush extends from the wiper element. The brush is used to sweep across other sensors in the sonde and thereby prevent the build-up of debris and growth that may interfere with accurate measurements. Typically, the sonde will be programmed to rotate the brush/wipe arm with sufficient frequency to keep the sensors clean enough to provide effective measurements.

In one embodiment, the wiper element and the brush rotate about a common axis. In accordance with a more particular embodiment of the invention, the wiper element and the brush are carried on a common arm that extends radially from a motor-driven shaft about which the arm rotates. In still a more preferred manifestation of the invention, the wiper media on the wiper element is formed from a foamed rubber pad and the brush is imitation squirrel hair.

Another manifestation of the invention is a sonde including a turbidity sensor and a pH sensor wherein the turbidity sensor includes a rotatable shaft that carries a wiper and a brush. The brush extends beyond the outer diameter of the turbidity sensor and rotates to wipe away and remove debris and growth from the pH sensor. In another manifestation of the invention, a sonde includes a turbidity sensor and an oxygen sensor constructed in the same manner as the foregoing.

Because of the self-wiping feature of the present invention, it is ideal for use in extended, long-term deployments. In addition, it is virtually maintenance-free. The wiped sensors dramatically increase deployment times without increased site visits or maintenance costs. As a result, time and money can be saved through the use of the present invention in extended deployment times and in severe fouling environments in conducting water quality tests.

DETAILED DESCRIPTION OF THE INVENTION

Figure 1:
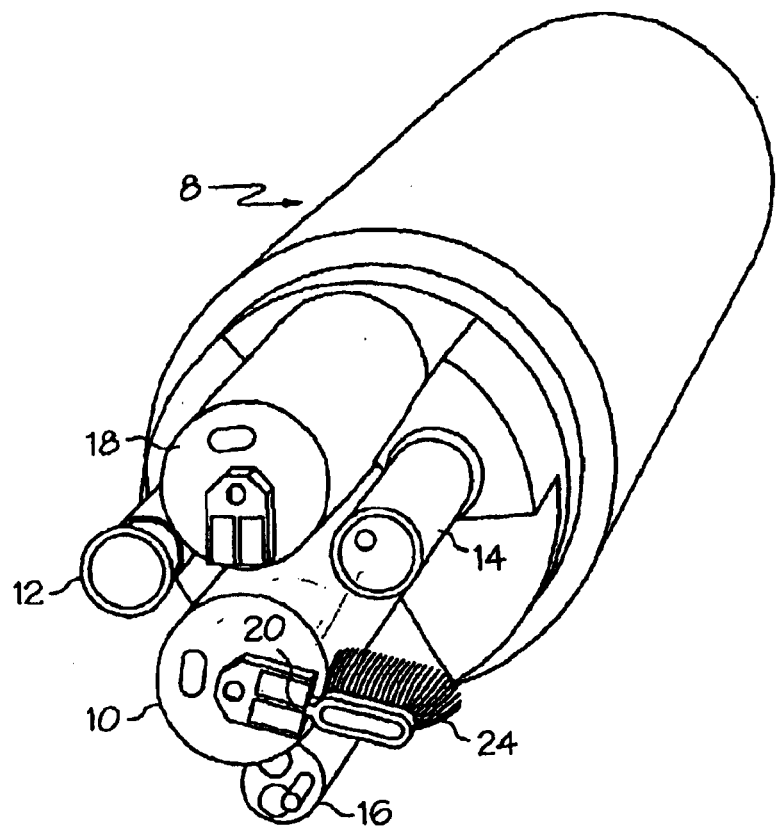
FIG. 1 is a view of the sensor cleaning apparatus in accordance with one embodiment of the invention
Figure 2:
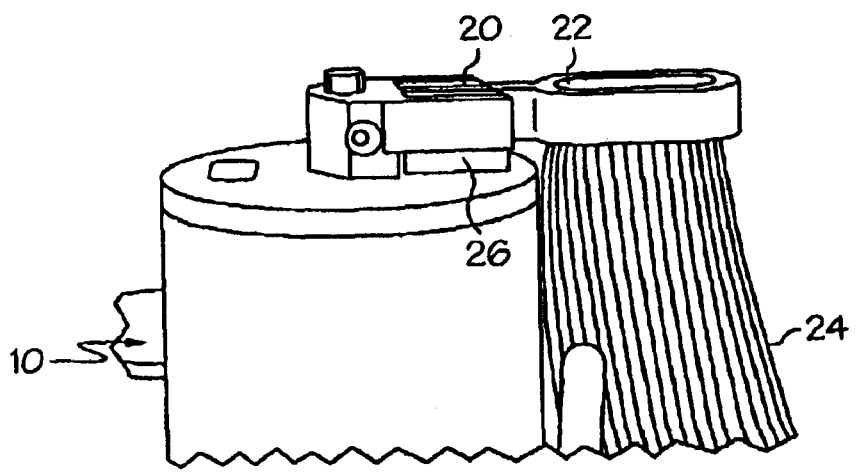
FIG. 2 is a view of the wiper element/brush assembly of the sensor cleaning apparatus in accordance with one embodiment of the invention

FIG. 1 is one example of a sonde in accordance with the invention. This sonde is now commercially available from YSI as the YSI Model 6600EDS Sonde. This sonde 8 includes a turbidity sensor 10 which measures turbidity as a function of backscatter, a dissolved oxygen sensor 12 which measures dissolved oxygen as a function of polarographic current, and a pH/ORP sensor 14 which measures pH as a function of electrical potential (voltage) relative to the potential of a reference electrode, a temperature/conductivity sensor 16 and a sensor 18, which can be a chlorophyll or rhomadine sensor. In accordance with the invention as shown in FIG. 2, the wiper element 20 includes a central arm 22 about which a wiper media 26 such as a foamed rubber wiper pad is wrapped. The portion of the arm 22 that extends beyond the diameter of the turbidity sensor 10 holds a brush 24. This brush 24 contains bristles which are long enough that they sweep across the other sensors in the sonde and prevent the build up of debris and growth.

In accordance with a preferred embodiment of the invention, the brush bristles are formed of a fine material which remains flexible after it has been wetted and dried. A particularly preferred material is imitation squirrel hair available from Felton Brush Company, Londonderry, N.H. However, those skilled in the art will recognize that other bristles such as goat hair might also be useful.

The results of extensive fouling may accumulate on a non-wiped sensor in an extended deployment and/or aggressive fouling environment. Extended deployments were conducted using the invention and the sensor cleaning device was used in an 80 day deployment; consistent measurements were able to be obtained throughout the 80 day period as a result of the sensor cleaning apparatus.

What is claimed:

1. A sonde comprising a first sensor and a second sensor adjacent the first sensor, the first sensor including an optical window and a wiper element, the wiper element rotating on a shaft extending from the first sensor so as to clean debris from the window, a brush extending from the wiper element beyond the perimeter of the first sensor such that the brush contacts the adjacent second sensor and removes debris which accumulates on the second sensor.

2. The apparatus of claim 1 wherein the first sensor is a turbidity sensor and the second sensor is selected from a pH sensor, a oxygen sensor, an ORP sensor, a chlorophyll sensor, a rhomadine sensor and a temperature/conductivity sensor.

3. The apparatus of claim 1 wherein the first sensor includes a rotatable shaft that carries the wiper element and the brush.

4. The apparatus of claim 1 wherein the brush comprises brush bristles.

5. The apparatus of claim 4 wherein the brush is formed from imitation squirrel hair.

6. The apparatus of claim 1 wherein the wiper element comprises a wiper media.

7. The apparatus of claim 6 wherein the wiper media is formed from a foamed rubber pad.

8. The apparatus of claim 1 wherein the wiper element and the brush rotate about a common axis.

9. The apparatus of claim 1 wherein the wiper element and the brush are carried on a common arm that extends radially a shaft about which the arm rotates.

10. A sonde comprising a first sensor and a plurality of sensors adjacent the first sensor, the first sensor including an optical window and a wiper element, the wiper element rotating on a shaft extending from the first sensor so as to clean debris from the window, a brush extending from the wiper element beyond the perimeter of the first sensor such that the brush contacts the adjacent multitude of sensors and removes debris which accumulates on the plurality of sensors.

11. The apparatus of claim 10 wherein the first sensor is a turbidity sensor and the plurality of sensors is selected from a pH sensor, a oxygen sensor, an ORP sensor, a chlorophyll sensor, a rhomadine sensor and a temperature/conductivity sensor.

12. The apparatus of claim 10 wherein the first sensor includes a rotatable shaft that carries the wiper element and the brush.

13. The apparatus of claim 10 wherein the brush comprises brush bristles.

14. The apparatus of claim 13 wherein the brush is formed from imitation squirrel hair.

15. The apparatus of claim 10 wherein the wiper element comprises a wiper media.

16. The apparatus of claim 15 wherein the wiper media is formed from a foamed rubber pad.

17. The apparatus of claim 10 wherein the wiper element and the brush rotate about a common axis.

18. The apparatus of claim 10 wherein the wiper element and the brush are carried on a common arm that extends radially a shaft about which the arm rotates.

* * * * *